United States Patent
Fleshner-Barak et al.

(10) Patent No.: US 7,195,778 B2
(45) Date of Patent: Mar. 27, 2007

(54) DRUG DELIVERY SYSTEM FOR ZERO ORDER, ZERO ORDER-BIPHASIC, ASCENDING OR DESCENDING DRUG DELIVERY

(75) Inventors: Moshe Fleshner-Barak, Petach Tikva (IL); E. Itzhak Lerner, Petach Tikva (IL); Vered Rosenberger, Jerusalem (IL)

(73) Assignee: Teva Pharmaceutical Industries Ltd., Petah Tigva (IL)

( * ) Notice: Subject to any disclaimer, the term of this patent is extended or adjusted under 35 U.S.C. 154(b) by 543 days.

(21) Appl. No.: 10/191,298

(22) Filed: Jul. 10, 2002

(65) Prior Publication Data

US 2003/0143257 A1    Jul. 31, 2003

Related U.S. Application Data

(60) Provisional application No. 60/303,809, filed on Jul. 10, 2001.

(51) Int. Cl.
*A61K 9/48* (2006.01)

(52) U.S. Cl. .................. 424/463; 424/400; 424/457; 424/452; 424/451

(58) Field of Classification Search ............... 424/468, 424/473, 474
See application file for complete search history.

(56) References Cited

U.S. PATENT DOCUMENTS

| | | | |
|---|---|---|---|
| 3,977,404 A | 8/1976 | Theeuwes | |
| 3,995,631 A | 12/1976 | Higuchi et al. | |
| 4,839,177 A | 6/1989 | Colombo et al. | |
| 5,156,850 A | 10/1992 | Wong et al. | |
| 5,422,123 A | 6/1995 | Conte et al. | |
| 5,681,584 A * | 10/1997 | Savastano et al. | 424/473 |
| 5,897,874 A | 4/1999 | Stevens et al. | |
| 6,200,600 B1 * | 3/2001 | Rashid | 424/451 |
| 6,303,144 B1 * | 10/2001 | Omura | 424/457 |
| 6,342,249 B1 * | 1/2002 | Wong et al. | 424/473 |
| 6,375,972 B1 | 4/2002 | Guo et al. | |

FOREIGN PATENT DOCUMENTS

WO    98/23263    6/1998

OTHER PUBLICATIONS

Laidler, P. et al., "What's New in Osmosin and Intestinal Perforation?" Path. Res. Pract., 180, 74-76 (1985).

* cited by examiner

*Primary Examiner*—Michael P. Woodward
*Assistant Examiner*—Eric E. Silverman
(74) *Attorney, Agent, or Firm*—Kenyon & Kenyon LLP (57) ABSTRACT

The invention is directed to a drug delivery device for controlled release of a drug, comprising a core that has a cylindrical plug embedded therein; and a coating that at least partially surrounds the core. The core is comprised of a drug and excipients. The coating surrounding the core is essentially impermeable to the drug. The cylindrical plug, which is embedded in the core, may be hollow or solid. The drug delivery device enables zero-order drug release profiles as well as more complicated release profiles to be obtained. The invention is also directed to a method of making the drug delivery device.

44 Claims, 7 Drawing Sheets

DRUG DELIVERY SYSTEM FOR ZERO ORDER, ZERO ORDER-BIPHASIC, ASCENDING OR DESCENDING DRUG DELIVERY

CROSS-REFERENCE TO RELATED APPLICATION

This application claims the benefit of provisional application Ser. No. 60/303,809, filed Jul. 10, 2001 which is incorporated herein by reference.

FIELD OF THE INVENTION

The present invention relates to a drug delivery device for oral administration of a drug. The drug delivery device provides controlled release of the drug.

BACKGROUND OF THE INVENTION

In the world of controlled release drug delivery systems there have been certain axioms upon which much development has been based. One such axiom is that 'flatter is better' i.e. the flatter the delivery curve is vs. time the better the system will behave. It is therefore considered desirable to have delivery systems that give essentially a zero order release profile. In drug delivery systems having a zero order release profile, the amount of drug released is not dependent on the amount left within the delivery system and remains constant over the entire delivery profile.

Tailoring the drug delivery to the needs of the therapy is another axiom of delivery improvement. One can conceive of therapies that need a sudden burst of drug after several hours of constant delivery or a change in the rate of drug delivery after several hours. A swelling hydrogel tablet delivery system or an eroding tablet delivery system, gives drug delivery that tapers off with time. In the eroding system, the surface that provides drug delivery is shrinking with time so the rate falls off proportionally. If the drug is delivered by diffusion through a non eroding hydrogel the rate falls off as drug depletion changes the force of the chemical gradient. These systems do not offer the opportunity to carefully tailor the drug release rates.

Zero order delivery has been achieved with the "Oros" osmotic pumps as is documented in many patents held by the Alza company (e.g. U.S. Pat. No. 3,995,631 to Higuchi, T. et. al., and U.S. Pat. No. 3,977,404 to Theeuwes, F.). The "Oros" system is based on osmotic pressure pushing the drug out of an almost microscopic orifice. The zero order profile is achieved due to the constant, small, cross section of the orifice being the rate determining step in the drug release. The "Oros" system has proven itself in several products but it has limitations. It is most useful for soluble drugs, with insoluble drugs having limited applicability. The technology of manufacture is somewhat complicated with the need of a laser drilled hole in the semipermeable coating. The drug release through an almost microscopic hole can also lead to several drawbacks. Clogging of the hole may limit drug release and the streaming of a concentrated solution of drug from the delivery system to the intestinal lumen can cause damage to the intestinal wall (see Laidler, P.; Maslin, S. C.; and Gihome, R. W. Pathol Res Pract 1985 180 (1) 74–76). Delays of the start of drug release can be achieved by coating the system (such as with an enteric coating) but the small orifice may be clogged by the coating and give erratic results in opening (if at all). The "Oros" system is best suited for a simple zero order delivery profile. Complicated patterns can be achieved with the "Oros" such as described in U.S. Pat. No. 5,156,850 to Wong, P. S. et. al. and in PCT WO 9823263 to Hamel, L. G. et. al., with concomitant complication of the manufacture and of the system, and without solving the drawbacks of the almost microscopic hole.

Zero order delivery profiles have been achieved with clever manipulation of the geometric surface of drug delivery as embodied in the "Geomatrix" delivery systems. (U.S. Pat. No. 4,839,177 to Colombo, P. et. al. and U.S. Pat. No. 5,422,123 to Conte, U. et. al.). These systems achieve a zero order profile by sandwiching the drug delivery layer between two layers that are impermeable. Only the drug delivery layer is eroded and the cross-section of the eroding layer is constant. Again here, there are several drawbacks. The manufacture of the system requires special equipment to produce two and three layer tablets. The system does not easily lend itself to changing the rate of delivery during the release profile. The amount of drug available in the tablet is somewhat limited since only one of the layers is used for drug delivery. The zero order profile may not be followed up to 100% of drug release due to tablet breakup once most of the central layer has eroded.

There is, therefore, still room for an improved zero order drug delivery system that is easy to manufacture, easy to control and allows one to make changes in the rate of drug delivery at a predetermined time in the release profile.

SUMMARY OF THE INVENTION

The invention is directed to a drug delivery device, comprising a core that has a cylindrical plug embedded therein; and a coating that at least partially surrounds the core. The core is comprised of a drug and excipients. The coating surrounding the core is essentially impermeable to the drug. The cylindrical plug, which is embedded in the core, may be hollow or solid.

The cylindrical plug expands upon absorbing the little water that permeates the coating, punching a hole in the impermeable coating. The hole that is formed is the size of the diameter of the solid cylindrical plug or the inner diameter of the hollow cylindrical plug. Thus, the hole is a macroscopic hole. The hole in the coating is filled with either the solid cylindrical plug or the hollow cylindrical plug. In the case of a solid cylindrical plug, water permeates into the cylindrical plug and drug permeates out of the cylindrical plug. Thus, drug release is very slow up until the point when the cylindrical plug falls out of the delivery device, as described below. In the case of a hollow cylindrical plug, drug release is effected by entry of water through the macroscopic hole to the core, causing drug dissolution or erosion and the exit of the drug solution or drug suspension through the same hole.

Drug dissolution or erosion is designed to be the rate determining step of drug release and is constant because of the constant cross section of the hole formed in the coating. In this way, the release of drug occurs at a constant, i.e., zero-order release, rate. The properties of the materials of which the cylindrical plug is made (i.e. how much axial swelling there is), as well as the geometry of the cylindrical plug, determine the size of the macroscopic hole and thus the rate of the zero order drug release. Changes in the rate of dissolution or erosion of the drug core can also effect the rate of drug release. Thus, it is also possible to obtain non-zero order release profiles, if so desired.

Non-zero order release profiles are easily attainable with the drug delivery device of the invention. Release delays may be obtained by coating the drug delivery device with an outer enteric coating. The enteric coating is applied over the impermeable coating in a smooth fashion. Release delays may also be obtained by varying the thickness of the impermeable coating. A thicker coating will delay the swelling of the cylindrical plug, thereby delaying drug release. The size of the cylindrical plug, and the nature of the excipients used to form the cylindrical plug, determines the rate of drug delivery from the drug delivery device and whether it provides a descending, ascending or zero order drug release profile. For example, once the cylindrical plug has burst through the coating, if the cylindrical plug continues to swell thereby making the diameter of the hollow cylindrical plug smaller with time, then a descending release profile will be observed. If, after the cylindrical plug bursts through the coating, it erodes or dissolves thereby making the diameter of the hole larger with time, then an ascending release profile will be observed. And, if after the cylindrical plug bursts through the coating and maintains its integrity, then a zero-order release profile will be observed.

Abrupt changes in the rate of drug release after a predetermined time can be brought about by having the cylindrical plug designed to fall out of the core after a certain period. The orifice of drug release will then grow considerably, allowing a more rapid drug release or a burst release to be appended to an extended zero order drug release profile. For example, if the outer diameter of the hollow cylindrical plug is 6 mm and the inner diameter is 3 mm, then the cross sectional area will grow four fold upon the plug falling out of the system. It is also possible to delay the release of drug by using a solid cylindrical plug. In which case, drug release is very slow or almost zero until the solid cylindrical plug falls out of the delivery device.

Figure 1:
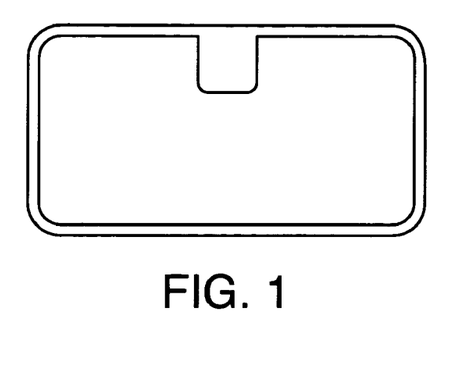
FIG. 1 shows shows a side view of a drug delivery device in accordance with the present invention.
Figure 2:
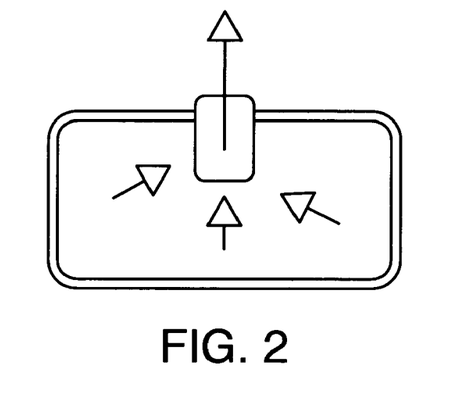
FIG. 2 shows a side view of a drug delivery device in accordance with the present invention, wherein the cylindrical plug has burst through the impermeable coating.
Figure 3:
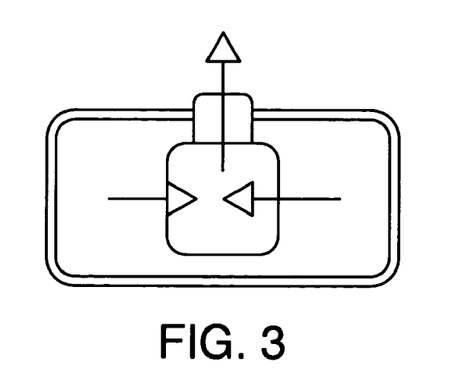
FIG. 3 shows a side view of a drug delivery device in accordance with the present invention, wherein a void has been formed in the drug core.

The drug delivery device may be made by forming a core comprising a drug and excipients, and embedding a cylindrical plug in the core. (FIG. 1). The core is then at least partially coated with a membrane that is essentially impermeable to the drug. This membrane serves to prevent any significant drug release from the surface of the drug delivery device. Small amounts of water do permeate the membrane causing the cylindrical plug to swell and burst the surface of the membrane. The result is a partially plugged hole of a defined geometry (FIG. 2). This hole is not a microscopic hole as in the osmotic pump systems. It is a macroscopic hole and its diameter is defined by the inner diameter of the hollow cylindrical plug or the diameter of the solid cylindrical plug. Water enters through the hole and dissolves drug from the core or erodes the core along with drug. The drug flows out of the system through the channel left in the cylindrical plug. As the drug delivery progresses a void may be formed in the core. This void will be filled with a pool of drug. The rate of drug release is, however, still controlled by the orifice (FIG. 3).

DETAILED DESCRIPTION OF THE INVENTION

The invention provides a drug delivery device for controlled release of the drug, comprising a drug core and a cylindrical plug embedded in the core. The core is at least partially coated with a coating which is essentially impermeable to the drug. The impermeable coating may be coated with a drug coating.

The core may be a standard pharmaceutical non-expanding core designed to dissolve or erode at a rate that is desired for the therapy at hand. Standard pharmaceutical excipients, such as, fillers, binders, diluents, disintegrants, lubricants, and wetting agents, may be used to form the core. Useful excipients include, but are not limited to, Nutab™ (sucrose), Polyethylene glycols (PEG), Microcrystalline cellulose, lactose, sodium lauryl sulfate, polyvinylpyrrolidone and mixtures thereof. One preferred composition of the core is: 53.9 wt. % Nutab™, 29 wt. % PEG 8000, 15 wt. % Avicel pH102™ (Microcrystalline cellulose), 1.1 wt. % Acetaminophen and 1 wt. % magnesium stearate. The diameter of the core preferably ranges from about 7 mm to about 15 mm, with about 9 to about 11 mm being more preferred. The drug content of the core can be from 0.1 to 99% by weight of the core, and the drug delivery device can be used to deliver essentially any drug for which oral administration is desired. Preferred drugs include acetaminophen, methylphenidate, oxybutynin, tizanidine and copaxone.

The cylindrical plug, which is preferably embedded at the surface of the core, may be solid or hollow. When the cylindrical plug is hollow, its outer diameter preferably ranges from about 5 to about 9 mm, with about 7 mm being more preferred. The inner diameter ranges from about 1 mm to about 6 mm, with about 2 mm to about 3 mm being most preferred for an outer diameter of about 7 mm. The cylindrical plug may be comprised of a material that further swells after the initial swelling or a material that erodes or dissolves upon contact with fluid after the initial swelling. The cylindrical plug may be in the form of a bi-layer tablet. One of the layers may be a placebo layer and the other layer may be a drug layer. Alternately, both layers may contain a drug. The drug in the cylindrical plug may be the same or different as that in the core. Additionally, each layer may contain a different drug.

Preferably, the excipients that form the cylindrical plug are excipients that can expand rapidly to break through the impermeable coating while keeping the form and shape of the cylindrical plug. Preferably, the cylindrical plug is comprised of a hydrogel. Examples of hydrogels which may be used to form the cylindrical plug include hydroxypropylcellulose, hydroxypropylmethylcellulose, methylcellulose, polyvinylpyrrolidone, polyethylene oxide, and mixtures thereof. Preferably, the cylindrical plug is further comprised of a superdisintegrant. Examples of superdisintegrants which may be used include croscarmellose sodium, crospovidone, sodium starch glycolate and mixtures thereof.

One preferred formulation of the cylindrical plug is: Hydroxypropylcellulose (Klucel MF) 35 wt. %, Methylcellulose 1500 34 wt. %, Crosscarmelose sodium 30 wt. % and Magnesium stearate 1 wt. %. Crosscarmellose sodium, which is a super disintegrant, serves to cause rapid swelling, while the hydrogel components prevent disintegration of the tablet and keep its geometric integrity.

Other excipients known in the art to posess these properties may be substituted for the preferred formulation as long as they serve to achieve the same function. Any superdisintegrant (e.g. crospovidone, sodium starch glycolate) may be substituted for the crosscarmelose and many combinations of hydrogel excipients chosen from the many grades of hydroxypropylcellulose, hydroxpropylmethylcellulose, polyvinylpyrollidone and other polysaccharides may be used. One versed in the art will know how to change the formulation to achieve more or less swelling, or more or less dissolution of the cylindrical plug during the drug release time.

The core containing the embedded cylindrical plug is coated with a coating which is essentially impermeable to the drug. The impermeable coating is preferably plasticized to a level that facilitates smooth coating but leaves the coat sufficiently rigid so that it bursts neatly. Examples of plasticizers that may be used include include triethylcitrate and polyethylene glycols. The grade of polymer and the amount of plasticizer can be determined by one skilled in the art by routine experimentation. Higher molecular weight polymers will need more plasticizer to keep them in the useful range of rigidity/plasticity. Typically, the plasticizer is present in an amount of from about 5–40 by weight of the polymer. A preferred coating comprises ethylcellulose having viscosity of 7 cps, plasticized with about 20% by weight of triethylcitrate. Another preferred coating comprises ethylcellulose having a viscosity of 7 cps plasticized with about 20% by weight of polyethylene glycol (PEG) 1000.

In a further embodiment, the impermeable coating may be coated with a drug coating. The drug coating may be one that dissolves quickly to provide an immediate pulse of the drug. Alternately, the drug coating may be one that erodes to provide a sustained release of the drug. The drug in the drug coating may be the same or different from the drug in the core. An example of a drug coating that dissolves quickly is one comprising Eudragit E (which dissolves readily in the stomach). An example of an eroding drug coating is one that comprises various grades of polyvinylpyrrolidone, hydroxypropyl cellulose or hydroxypropylmethylcellulose, optionally including a plasticizer(s) known in the art.

In another embodiment the cylindrical plug can contain a dose of the same or a different drug as that in the core. This dose can be designed to be delivered slowly from the cylindrical plug by diffusion or erosion. This delivery device can also be further coated with a drug coating as described above.

In another embodiment, the solid cylinder is a bilayer tablet, where one layer expands upon absorbing moisture and bursts through the impermeable coating, while the second layer releases a drug (which can be the same or different as that in the core). The drug may be released in a delayed fashion, the delay being the time needed for the bi-layer tablet to burst the impermeable coating. Or the drug may be released in a sustained fashion. This delivery device can also be further coated with a drug coating as described above.

In a preferred embodiment, methylphenidate is incorporated into the core. The core is comprised of about: 1–10 wt. % drug; 1–20 wt. % microcrystalline cellulose; 60–90 wt % sucrose; and 0.2–2 wt. % of a lubricant, such as magnesium stearate. The core has a solid cylindrical plug embedded therein. The solid cylindrical plug is in the form of a bi-layer tablet. One of the layers comprises about: 1–30 wt. % methylphenidate; 60–95 wt. % lactose; 0–5 wt. % microcrystalline cellulose; and 0.2–2 wt. % lubricant. The other layer, which is the expanding layer that bursts through the impermeable coating, comprises about: 20–50 wt. % hydroxypropylcellulose HF, 20–50 wt. % methylcellulose 1500, 25–40 wt. % croscarmellose sodium and 0.2–1 wt. % lubricant. The cylindrical plug is pressed into the surface of the core and the ensemble is coated with an impermeable coating. The impermeable coating is comprised of about 5–10 mg per tablet of ethylcellulose (Ethocel 7 cps) plasticized with about 20 wt. % triethylcitrate. The impermeable coating is then overcoated with a coat comprising Eudragit E and 0–50 wt. % methylphenidate. Thus, this drug delivery device provides three different doses of methylphenidate. The first dose is an immediate release dose from the outermost (Eudragit E) coat. The second dose is a short controlled release dose (one to two hours in duration). The third dose is an extended release dose from the core after the solid cylindrical plug has fallen out. This dose lasts for about 8–12 hours.

In a more preferred embodiment, the core comprises about: 7 wt. % methylphenidate; 10 wt. % microcrystalline cellulose; 82 wt. % sucrose; and 1 wt. % magnesium stearate. The cylindrical plug is a bi-layer tablet, wherein one of the layers is a drug layer and the other layer is an expanding layer. The drug layer weighs about 35 mg and comprises about: 24 wt. % methylphenidate; 70 wt. % lactose; 5 wt. % microcrystalline cellulose; and 1 wt. % magnesium stearate. The expanding layer weighs about 45 mg and comprises about: 35 wt. % hydroxypropylcellulose HF, 34 wt. % methylcellulose 1500; 30 wt. % croscarmellose sodium; and 1 wt. % magnesium stearate. The cylindrical plug, which has a diameter of about 5 mm, is pressed into the surface of the core and the ensemble is coated with an impermeable coating comprised of about 8 mg per tablet of ethylcellulose (Ethocel 7 cps) plasticized with about 20 wt. % triethylcitrate. This impermeable coating is then over coated with about 18 mg of a drug layer comprised of about: 67 wt. % Eudragit E and 33 wt. % methylphenidate. The entire drug delivery device is an 8 mm tablet weighing about 425 mg.

In yet another embodiment, the core can be a bilayer tablet, wherein each layer contains the same or different drug. Alternately, the upper layer can be a placebo layer to provide either a delay before drug delivery (in the case of the placebo layer) or sequential delivery of two different drugs with independent release profiles or two different release profiles of the same drug.

In a preferred embodiment, a drug may be incorporated into the lower layer of the core, while the other layer comprises a slowly eroding placebo formulation. The drug layer provides a delayed dose of the drug and may be a slow release zero order formulation or may be of short duration slow release so that it approximates a drug burst. The cylindrical plug is a solid cylindrical plug comprised of a placebo formulation. A first dose of drug is provided by coating the impermeable coat with a drug containing overcoat.

In a more preferred embodiment, the core is comprised of two layers. The lower layer comprises about 2 to about 36 mg tizanidine. This layer may be formulated to release the drug in a sustained or immediate fashion. The upper layer comprises excipients that are eroded slowly over several hours. For example, the upper layer may comprise sucrose, polyvinylpyrrolidone K-30, lactose and similar excipients.

In a most preferred embodiment, the core has two layers: the upper layer weighs about 210 mg and comprises about 89 wt. % sucrose, about 10 wt. % polyvinylpyrrolidone, and about 1 wt. % magnesium stearate; and the lower layer contains tizanidine and excipients. The solid cylindrical plug is about 5 mm in diameter and weighs about 50 mg. The cylindrical plug comprises about 37 wt. % hydroxypropylcellulose HF, about 34 wt. % methylcellulose 1500, about 28 wt. % croscarmellose sodium and about 1 wt. % magnesium stearate. The solid cylindrical plug is pressed into the upper layer of the core and the entire ensemble is coated first with an impermeable coat of ethylcellulose and then with an overcoat comprised of Eudragit E and about 2 to 8 mg tizanidine. The drug overcoat dissolves readily in gastric fluid giving an immediate burst of tizanidine. The second dose of tizanidine is delayed several hours before it is delivered.

Thus, the drug delivery device is capable of providing various release profiles, including a zero order drug release profile, a biphasic drug release profile, a triphasic drug release profile, an ascending drug release profile, or a descending drug release profile.

The invention further provides a method of making a drug delivery device by forming a core comprised of a drug and excipients; embedding a cylindrical plug in the core; and at least partially coating the core with a coating which is essentially impermeable to the drug.

The cylindrical plug may be formed using standard tableting machines with a punch of proper design. It may be formed by direct compression or standard granulation techniques. The cylindrical plug may be comprised of two layers. One of the layers may be a placebo layer and the other layer may be a drug layer. Alternately, both layers may contain a drug. The drug in the cylindrical plug may be the same or different as that in the core. Additionally, each layer may contain a different drug.

The core, with the cylindrical plug embedded therein, may be produced in a standard press coat tableting machine (e.g. Killian RUD or equivalents). The cylindrical plug is fed as a preformed plug and the core formulation is fed as a mixture of powders or as a granulate. The press coat tableting machine is operated with the inner tablet off center to place it at the surface of the core. The entire assembly is coated with an impermeable coating such as ethylcellulose or Eudragit RS.

In one embodiment, the core is a bi-layer tablet where the lower layer is the drug containing layer and the upper layer is a placebo layer. The cylindrical plug is embedded at the surface of the upper layer. In this embodiment, the core is produced in a press coating tableting machine (Kilian RUD) modified to have two powder adding stations before the tablet adding station (so that the tablet is at the surface and not in the center of the tablet as in a "press coated" tablet) and fitted with normal concave punches. The lower layer is formed by blending the drug and excipients and filling the mixture into the die at the first fill station. The upper layer is formed by blending the appropriate excipients and feeding the mixture at the second station. The delay in the release of the drug in the lower layer can be controlled by adding more or less of the mixture which forms the upper placeble layer to the second fill station. The cylindrical plug is then fed as a preformed tablet at the third station using the Kilian RUD automatic mechanism for adding preformed tablets to the powder bed.

Having thus described the invention with reference to certain preferred embodiments, it is further illustrated by the following non-limiting examples.

EXAMPLE 1

Zero Order Release:

Formation of Hollow Cylindrical Plug:

The hollow cylindrical plug was formed by mixing the excipients in Table 1 in a plastic bag for about 5 minutes. Magnesium Stearate (1 wt. %) was then added and the mixture mixed for a further one minute. The cylindrical plug was formed in a Manesty F3 single punch tableting machine using a punch that gives the geometry in Table 2.

TABLE 1

| Material | Weight Percent |
| --- | --- |
| Hydroxypropylcellulose (Klucel MF) | 35 |
| Methylcellulose 1500 | 34 |
| Croscarmelose Sodium | 30 |

TABLE 2

| Height | 2.9 mm |
| --- | --- |
| Diameter | 7 mm |
| Inner Diameter | 3.5 mm |

Formation of Core:

The core was formed by mixing the excipients and drug shown in Table 3 for about five minutes in a plastic bag. Magnesium Stearate (1 wt. %) was then added and the mixture mixed for another minute. The drug delivery device was formed using a Manesty F3 single punch fitted with a 10 mm diameter normal concave punch by filling with the excipient and active mixture, placing the hollow cylindrical plug on the mixture, and pressing. Drug delivery devices were obtained that had the physical characteristics described in Table 4.

TABLE 3

| Material | Weight Percent |
| --- | --- |
| Sucrose (Nutab ™) | 53.9 |
| PEG 8000 | 29 |
| Microcrystalline cellulose (Avicel pH102) | 15 |
| Acetaminophen | 1 |

TABLE 4

| Weight | 570 mg |
| --- | --- |
| Height | 5.6 mm |
| Diameter | 10 mm |
| Hardness | 10.3 kp |

Coating:

The drug delivery device was coated with a coat of ethylcellulose using the conditions in Table 5:

TABLE 5

| | |
|---|---|
| Ethylcellulose concentration | 3% w/w |
| Triethylcitrate (plasticizer) Concentration | 0.6% w/w |
| Flow rate | 1.6 ml/min |
| Air pressure | 0.5 bar |
| Bed temperature | 36–45° C. |

The ethylcellulose coating was about 14–18 mg /tablet.

Figure 4:
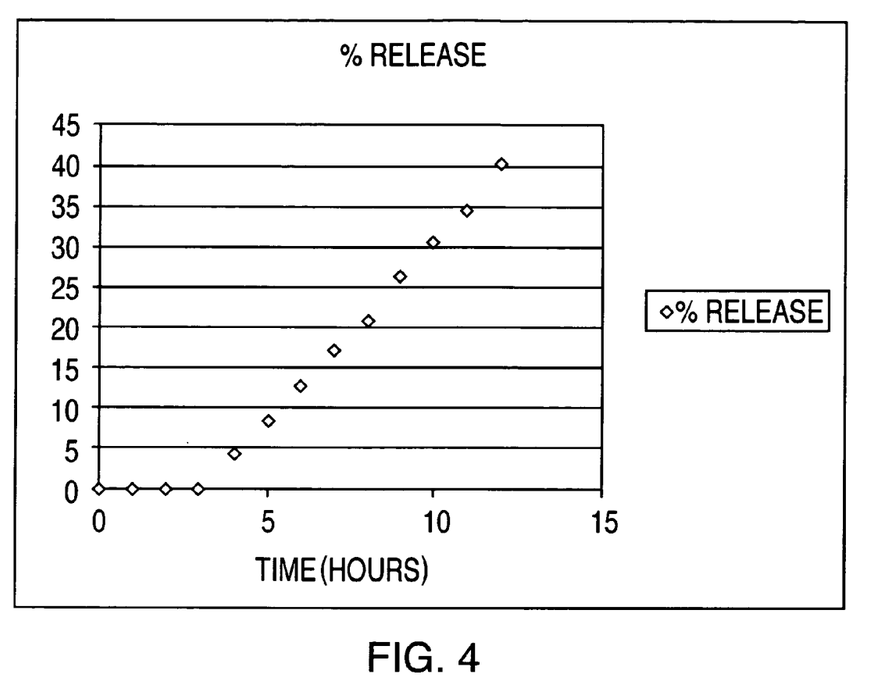
FIG. 4 shows the in vitro release profile of acetaminophen from a drug delivery device made according to Example 1.

In Vitro Release:

The in vitro release was measured in 900 ml of water in a dissolution bath at 37 degrees and 100 RPM. The amount of acetaminophen released was measured by UV at 243 nm. A clear zero order release profile for 4–12 hours with a release rate of about 5% per hour, is obtained. The results are shown in Table 6 and in FIG. 4.

TABLE 6

| time | % Release |
|---|---|
| 0 | 0 |
| 1 | 0 |
| 2 | 0 |
| 3 | 0 |
| 4 | 4.41 |
| 5 | 8.63 |
| 6 | 12.92 |
| 7 | 17.38 |
| 8 | 20.79 |
| 9 | 26.61 |
| 10 | 30.75 |
| 11 | 34.69 |
| 12 | 40.48 |

EXAMPLE 2

Zero Order Release:

Formation of Hollow Cylindrical Plug:

A hollow cylindrical plug was formed by mixing the excipients shown in Table 7 in a plastic bag for 5 about minutes. Magnesium Stearate (1 wt. %) was then added and the mixture mixed for another minute. The cylindrical plug was pressed in a Manesty F3 single punch tableting machine using a punch that gives the geometry in Table 8.

TABLE 7

| Material | Weight Percent |
|---|---|
| Hydroxypropylcellulose (Klucel HF) | 50.3 |
| Hydroxypropylmethylcellulose (Methocel K-15) | 16.7 |
| Croscarmelose Sodium | 22 |
| Tannic Acid | 10 |

TABLE 8

| | |
|---|---|
| Height | 2.9 mm |
| Diameter | 7 mm |
| Inner Diameter | 3.5 mm |

Formation of Core:
  Same as Example 1

Coating:
  Same as Example 1

In Vitro Release:
  Same as Example 1

Results

Figure 5:
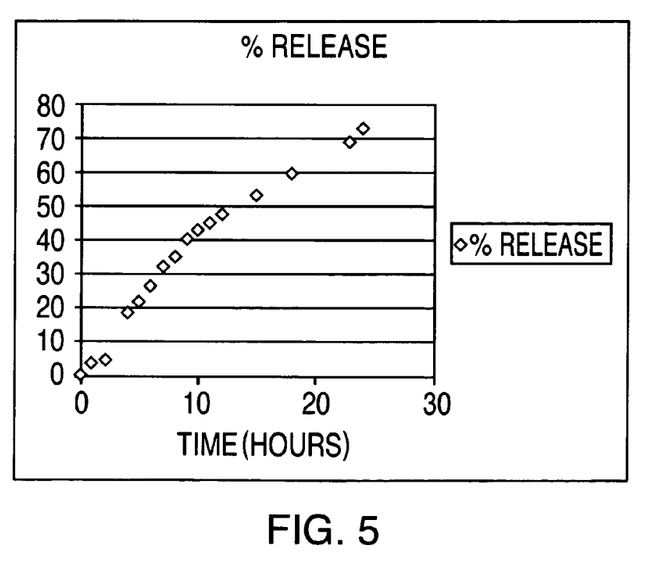
FIG. 5 shows shows the in vitro release profile of acetaminophen from a drug delivery device made according to Example 2.

The results of the in vitro release are given in Table 9 and FIG. 5.

TABLE 9

| time | % Release |
|---|---|
| 0 | 0 |
| 1 | 3.3 |
| 2 | 4.59 |
| 4 | 18.57 |
| 5 | 22.35 |
| 6 | 26.38 |
| 7 | 32.26 |
| 8 | 35.62 |
| 9 | 40.26 |
| 10 | 43.19 |
| 11 | 45.24 |
| 12 | 47.82 |
| 15 | 53.22 |
| 18 | 60.2 |
| 23 | 69.38 |
| 24 | 73.86 |

As shown in Table 9, an essentially zero order drug release pattern over 24 hours with a release rate of about 3% per hour is obtained. The hollow cylindrical plug in this example was designed to swell to a larger extent than the one in Example 1 by changing the formulation of the cylindrical plug. The larger swelling leads to earlier drug release (earlier breach of the impermeable ethylcellulose coating) and to a slower release rate. The inner diameter of the cylindrical plug is made smaller by the swelling of the material. The smaller diameter of the channel in the cylindrical plug gives a lower release rate of the soluble drug.

EXAMPLE 3

Biphasic Release

Formation of Hollow Cylindrical Plug:
  Same as in Example 1

Formation of Core:

The core was formed by mixing the excipients and drug shown in Table 10 for five minutes in a plastic bag. Magnesium Stearate (1 wt. %) was then added and the mixture mixed for another minute. The drug delivery device was formed using a Manesty F3 single punch fitted with a 10 mm diameter normal concave punch by filling with the excipient and active mixture, placing the hollow cylindrical plug on the mixture, and pressing. A drug delivery device was obtained that had the physical characteristics described in Table 11.

TABLE 10

| Material | Weight % |
|---|---|
| Sucrose (Nutab ™) | 40.5 |
| PEG 4000 | 24.6 |
| Sodium Lauryl Sulfate (SLS) | 5.0 |
| Povidone K-30 | 5.0 |
| 75% Lactose/ 25% Cellulose(Cellactose 80 ™) | 22.8 |
| Acetaminophen | 1.1 |

TABLE 11

| | |
|---|---|
| Weight | 535 mg |
| Height | 6.3 mm |
| Diameter | 10 mm |
| Hardness | 7.4 kp |

Coating:

Same as Example 1

In vitro Release:

Same as Example 1

Results

Figure 6:
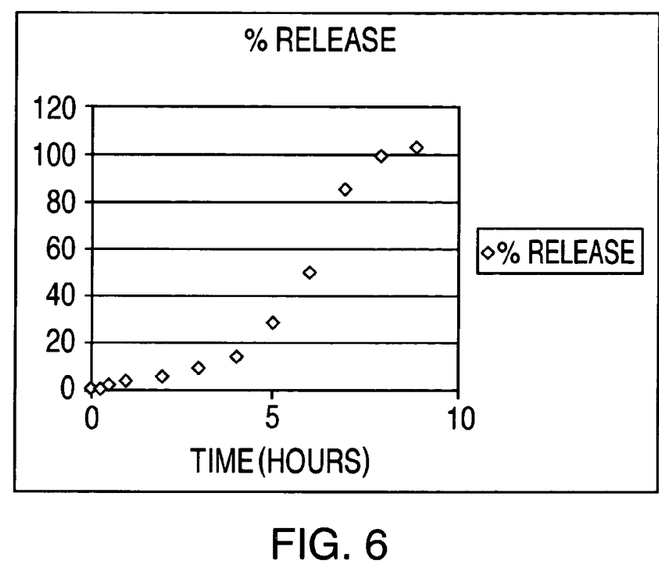
FIG. 6 shows shows the in vitro release profile of acetaminophen from a drug delivery device made according to Example 3.

The results of the in vitro release are given in Table 12 and FIG. 6.

TABLE 12

| time | % Release |
|---|---|
| 0 | 0 |
| 0.25 | 0.31 |
| 0.5 | 1.35 |
| 1 | 2.86 |
| 2 | 5.03 |
| 3 | 8.6 |
| 4 | 12.96 |
| 5 | 28.12 |
| 6 | 49.55 |
| 7 | 84.93 |
| 8 | 99.01 |
| 9 | 102.16 |

As shown in Table 12, a zero order release rate similar to that in example 2 for the first four hours followed by an accelerated rate of release, is obtained. The hollow cylindrical plug fell out of the tablet after four hours, thus widening the opening for drug release from ~3.5 mm (the exact diameter is somewhat different due to the swelling of the formulation of the cylindrical plug) to 7 mm. The formulation of the core, specifically the SLS in the formulation, leads to the cylindrical plug falling out after a predetermined time.

EXAMPLE 4

Biphasic Release

Formation of Hollow Cylindrical Plug:

Same as in Example 1

Formation of Core

The core was formed by mixing the excipients and drug in Table 13 for five minutes in a plastic bag. Magnesium Stearate (1 wt. %) was then added and the mixture mixed for another minute. The drug delivery device was formed using a Manesty F3 single punch fitted with a 10 mm diameter normal concave punch by filling with the excipient and active mixture, placing the hollow cylindrical plug on the mixture, and pressing. A drug delivery device was obtained that had the physical characteristics described in Table 14. In this example Oxybutynin chloride was used as an active in place of Acetaminophen.

TABLE 13

| Material | Weight % |
|---|---|
| Sucrose (Nutab ™) | 38.5 |
| PEG 4000 | 30.0 |
| Sodium Lauryl Sulfate (SLS) | 8.0 |
| Povidone K-30 | 20.0 |
| Oxybutynin chloride | 2.5 |

TABLE 14

| | |
|---|---|
| Weight | 610 mg |
| Height | 6.4 mm |
| Diameter | 10 mm |
| Hardness | 7.3 kp |

Coating:

Same as Example 1

In vitro Release:

Same as Example 1

Results

Figure 7:
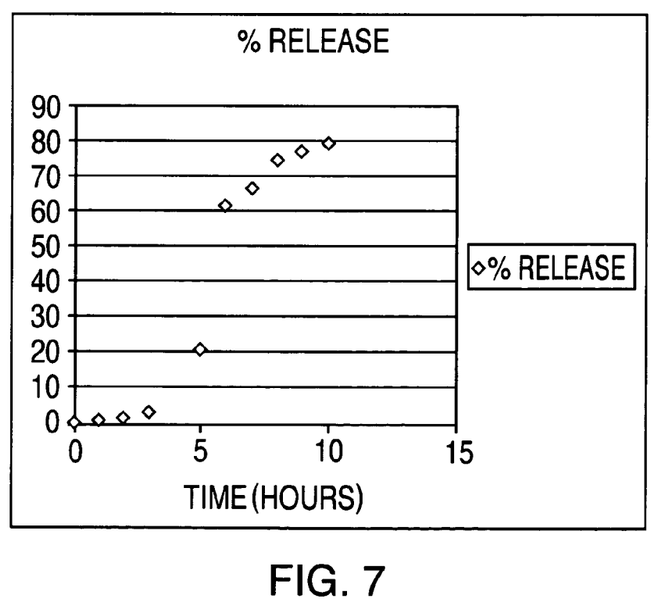
FIG. 7 shows shows the in vitro release profile of oxybutynin chloride from a drug delivery device made according to Example 4.

The results of the in vitro release are given in Table 15 and FIG. 7.

TABLE 15

| time | % Release |
|---|---|
| 0 | 0 |
| 1 | 1.33 |
| 2 | 2 |
| 3 | 3.67 |
| 5 | 20.83 |
| 6 | 61 |
| 7 | 66.83 |
| 8 | 74.67 |
| 9 | 77.33 |
| 10 | 79.33 |

As shown in Table 15, a slow release the first three hours followed by a rapid burst of drug and then a rapid release phase to the finish of the drug release, is obtained. Again here, SLS in the formulation leads to the cylindrical plug falling out after a predetermined time, providing a more rapid drug release.

EXAMPLE 5

Triphasic Release of Methylphenidate

The Concept

To obtain triphasic release there needs to be three reservoirs of the drug. The first reservoir must be capable of immediate release while the next two reservoirs are delayed release. The first of the delayed release doses has a relatively short release period while the last, main reservoir, provides an extended release. To achieve this profile the following delivery system was developed, using the invention described herein. The first dose of drug is delivered from an outer overcoat that is readily soluble in gastric fluid. This coat contains about 6 mg of drug. The cylindrical plug that bursts through the impermeable membrane is a solid, bi-layer cylindrical plug. The upper layer is a swelling layer that bursts through the impermeable coating while the lower layer contains another dose of about 6–7 mg of the drug. The core is the main reservoir of drug, containing about 23 mg of the drug. The core is designed to give a zero order extended release through the hole made by the bi-layer embedded solid cylindrical plug. When the system is placed in gastric fluid the overcoat dissolves immediately giving a first dose of immediate release. There is a delay while the embedded cylindrical plug swells and punctures the impermeable coat. The drug dose contained in the lower layer of the embedded cylindrical plug is released over a short period (½ to 2 hours). The drug in the core starts to release. The drug in this reservoir is released over 6–8 hours in a zero order fashion.

The Cylindrical Plug

The cylindrical plug was a bi-layer 5 mm flat beveled tablet produced using a Kilian RUD tablet press. The drug layer was prepared by first granulating methylphenidate with lactose and then blending with microcrystalline cellulose and subsequently magnesium stearate. The granulation was carried out by blending 150 parts lactose (DMV International) with 50 parts methylphenidate (Mallinkrodt Inc.) on a Zanchetta Rotolab 0machine. Water (20 parts) was added to wet the mass while mixing at 350 rpm and then at 500 rpm. The mass was milled through a 1.6 mm screen (Erweka), dried in a fluidized bed drier (Aeromatic Laboratory Drier) at 40 C. to a moisture content of <1.5%, and milled again through a 0.8 mm screen. This granulate, 94 parts, was blended with 5 parts microcrystalline cellulose (Avicel™ pH102 FMC International) for several minutes, then one part of magnesium stearate NF/EP (Mallinkrodt Inc.) was added and blended for another minute. The swellable gel layer was formed by blending 35.2 parts hydroxypropylcellulose (Klucel HF, Aqualon Ltd.), 34.2 parts methylcellulose 1500(Dow Chemical Inc.), and 30.1 parts croscarmellose sodium (AC-DI-SOL, FMC International) for 5 minutes. Magnesium stearate at 0.5 parts was added and the blend mixed for a further minute. The drug containing layer weighed 30 mg while the swelling layer weighed 45 mg. The tablets had a hardness of about 3–6 kP. The drug content of the drug layer was 7 mg.

The Core

The core was formed by pressing the bi-layer solid cylindrical plug into a blend of methylphenidate and excipients. The blend was formed by mixing 6.6 parts of methylphenidate, 10.0 parts of microcrystalline cellulose, and 82.4 parts compressible sucrose (Nutab™ DMV International) for several minutes, adding 1 part magnesium stearate, and mixing for one minute. The tablets were compressed using a Manesty F3 single punch machine, fitted with 8 mm flat beveled punches, with manual placement of the preformed bi-layer cylindrical plug in the powder bed. The drug delivery device (the bi-layer cylindrical plug embedded at the surface of the core) had a diameter of 8 mm, a weight of 425 mg and a hardness of 17–20 kP. The drug content of the core was 23 mg.

The Drug Delivery Device

The drug,delivery device was coated with an insoluble coating in an Erweka coating pan heated with an air gun. The first coating solution was 3.0% ethylcellulose (Ethocel 7 cps Dow Chemical Inc.) and 0.6% triethyl citrate (Rhom Pharma Ltd.) in ethanol. The solution was sprayed through a 1 mm nozzle using 0.5 bar atomizing air with a solution flow of 1–2 ml/min. The solution flow was varied to prevent sticking of the drug delivery device and to keep the temperature of the tablet bed between 35–40° C. The spraying process was stopped at a weight gain of 7–9 mg per drug delivery device forming the impermeable coat. A drug overcoat was formed on the insoluble coating. The drug overcoat was comprised of a solution of 2.5 wt. % Eudragit E100 (Rhom Pharma Ltd.) and 1.25 wt. % methylphenidate dissolved in ethanol. This solution was sprayed onto the ethylcellulose coated drug delivery devices to a weight gain of 18 mg, giving a drug content of 6 mg for this layer.

Results

Figure 8:
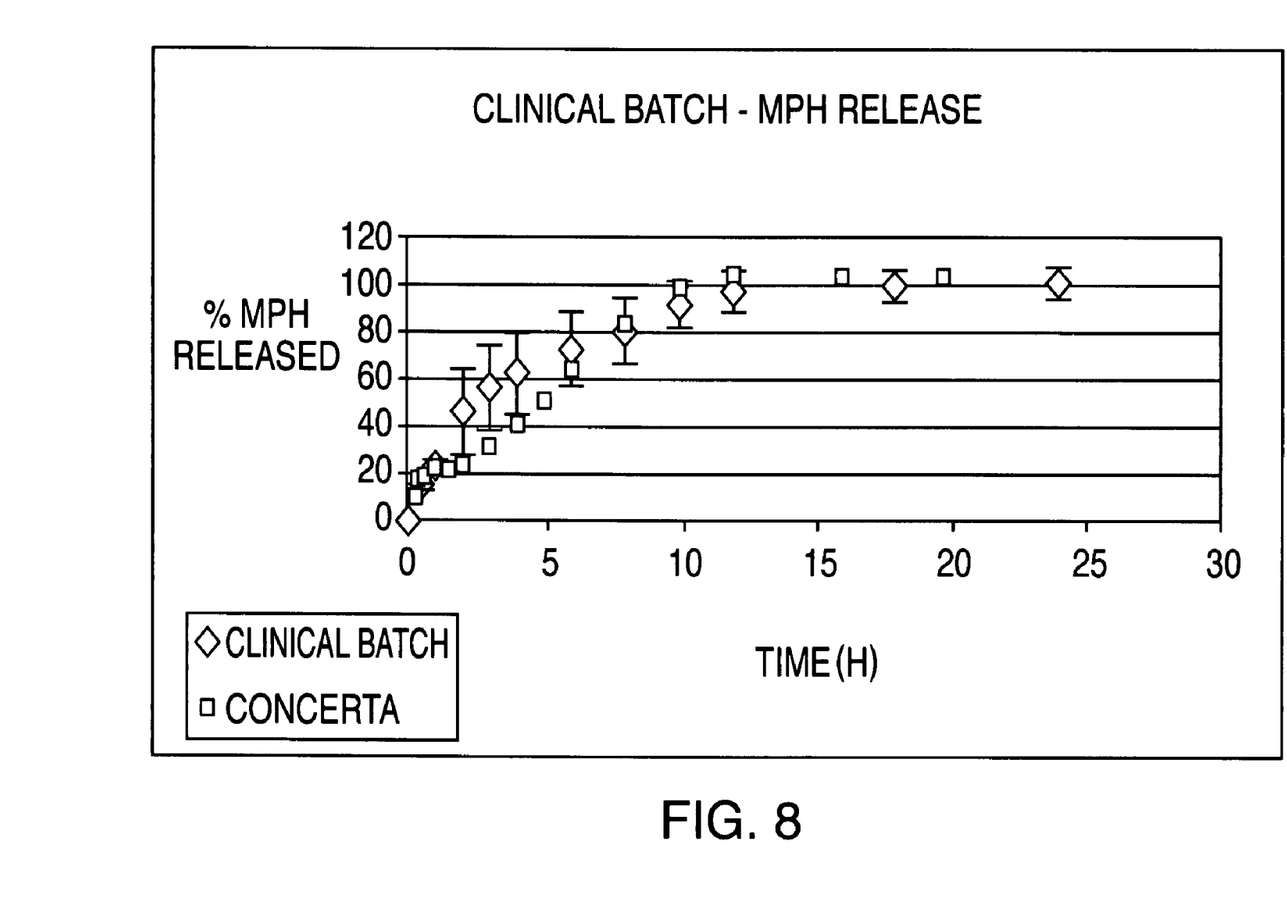
FIG. 8 shows a comparison of the in vitro release profile of methylphenidate from a drug delivery device made according to Example 5 to that of the commercial product Concerta®.

The drug delivery device was tested in a Hanson dissolution bath at 37 C in 900 ml of media. The first two hours were tested in 0.1N HCl. After two hours the drug delivery device was transferred to distilled water. The methylphenidate in the device was determined by an HPLC method on a cyano column using an aqueous buffer (pH 4): acetonitrile system with UV detection at 210 nm. The results are shown in Table 16 and in FIG. 8. FIG. 8 shows a comparison of the release profile obtained with the drug delivery device of Example 5 to that of the commercial methylphenidate product Concerta®. The profile shows an immediate release, followed by a delay and then an extended release profile which has a slower and then a faster portion. The in vitro release profile for the device in Example 5 shows the same elements. An initial burst is seen immediately followed by another burst of drug at two hours. This is then followed by an essentially zero order drug release up to 8 to 10 hours.

TABLE 16

Release Profile of methylphenidate in vitro

| time (h) | vessel 1 | vessel 2 | vessel 3 | vessel 4 | vessel 5 | vessel 6 | Average | Stdev |
|---|---|---|---|---|---|---|---|---|
| 0 | 0 | 0 | 0 | 0 | 0 | 0 | 0.0 | 0.0 |
| 0.5 | 11.8 | 18.7 | 18.7 | 13.4 | 15.2 | 19 | 16.1 | 3.1 |
| 1 | 21.9 | 22.4 | 19.3 | 22.8 | 28.3 | 21.6 | 22.7 | 3.0 |
| 2 | 63.8 | 38.7 | 22.4 | 55.4 | 65.1 | 29.9 | 45.9 | 18.1 |
| 3 | 72.5 | 44.5 | 28 | 67.2 | 73.9 | 51 | 56.2 | 18.2 |
| 4 | 76.7 | 50.7 | 32.6 | 72.4 | 77.6 | 63.4 | 62.2 | 17.7 |
| 6 | 83.1 | 73.8 | 41.7 | 79 | 84.4 | 74.1 | 72.7 | 15.8 |
| 8 | 87.1 | 87.8 | 52.3 | 85.5 | 90.2 | 79.8 | 80.5 | 14.2 |
| 10 | 98.3 | 95.6 | 73.1 | 93.5 | 99.8 | 90.4 | 91.8 | 9.7 |
| 12 | 98.9 | 110.3 | 84.2 | 95.2 | 101.1 | 92.9 | 97.1 | 8.7 |
| 18 | 99.7 | 112 | 96 | 95.2 | 101.1 | 92.9 | 99.5 | 6.8 |
| 24 | 104.2 | 112 | 99.5 | 95.2 | 101.1 | 92.9 | 100.8 | 6.8 |

Thus, the drug delivery device of the invention has been shown to be capable of generating complicated delivery patterns in vitro. In the case of Example 5, it delivers two bursts of drug delayed by about 1 hour, followed by a zero order release of the drug up to 8–10 hours.

EXAMPLE 6

Delayed $2^{nd}$ Dose of Tizanidine

The Concept

To obtain a delayed second dose of a drug after an immediate release dose, two reservoirs of drug are necessary. The immediate release layer is contained in an outer overcoat as in Example 5. The second dose of drug may be in the cylindrical plug or in the core Placing the second dose in the core allows more flexibility in designing the length of the delay. To obtain the ability to control the delay the cylindrical plug is a solid swelling plug while the core is a bi-layer tablet. The upper layer is a placebo layer that erodes at a predetermined rate depending on its formulation and the size of the hole punched in the impermeable coat. Alternately, the thickness of the placebo layer can be the determining factor in the delay time. Beneath this layer is the drug layer which releases the drug in a short, controlled release pattern.

The Cylindrical Plug

The cylindrical plug was formed by pressing a blend of excipients in a Manesty F3 single punch tableting machine fitted with 5 mm flat faced punches. The blend was formed by mixing 37.1 parts hydroxypropylcellulose (Klucel HF, Aqualon Ltd), 34.5 parts methylcellulose 1500 (Dow Chemical Inc.), and 27.4 parts croscarmellose sodium (AC-DI-SOL, FMC International) for five minutes. 1.0 part of magnesium stearate NF/EP (Mallinkrodt Inc.) was added and the blend mixed for another minute. The cylindrical plug weight was 50 mg and its hardness was 2–6 kP.

The Core

The core is a bi-layer tablet where the lower layer is the drug containing layer and the upper layer is a placebo layer. The cylindrical plug is embedded at the surface of the upper layer. The core was produced on a Kilian RUD tablet machine modified to have two powder adding stations before the tablet adding station (so that the tablet is at the surface and not in the center of the tablet as in a "press coated" tablet) and fitted with 9 mm normal concave punches. To form the lower layer, a blend of 40 parts tizanidine (Farmac Co. Ltd.) powder, 30 parts microcrystalline cellulose (Avicel™ pH101 FMC International), and 30 parts xylitol (Danisco Sweeteners OY) were granulated with water (5 parts) in a Diosna P1/6 granulator. The granulate was dried in a fluidized bed drier (Aeromatic Laboratory Drier) at 40° C. until the moisture content was <1.7%. The dry granulate was milled through a 0.8 mm screen. The granulate, 6.6 parts, was mixed with 50 parts compressible sucrose (Nutab™ DMV International), 10 parts microcrystalline cellulose (Avicel™ pH101 FMC International, 22.4 parts xylitol and 10 parts crospovidone NF (BASF Pharma) and subsequently with one part magnesium stearate. 150 mg of this blend was filled into the die at the first fill station. The placebo layer was formed from a blend of 89 parts compressible sucrose (Nutab™ DMV International ), 10 parts polyvinylpyrollidone (Povidone k-30, ISP Switzerland AG) and 1 part magnesium stearate. 200 mg of this blend was fed at the second station for a 3 hour delay and about 300 mg was fed at this station to obtain a 6 hour delay. The cylindrical plug was fed as a preformed tablet at the third station using the Kilian RUD automatic mechanism for adding preformed tablets to the powder bed. The final tablet was of 9 mm diameter, had a hardness of 10–20 kP and weighed 400 mg for a 3 hour delay and 500 mg for a six hour delay. The core contained 4 mg tizanidine.

The Drug Delivery Device

The tablets were coated with an insoluble coating in an Erweka coating pan heated with an air gun. The insoluble coating solution was 3.0% ethylcellulose (Ethocel 7 cps Dow Chemical Inc.) and 0.6% polyethylene glycol (PEG 1000 Clariant Hoechst Ltd.) in ethanol. The solution was sprayed through a 1 mm nozzle using 0.5 bar atomizing air with a solution flow of 1–2 ml/min. The solution flow was varied to prevent sticking of the tablets and to keep the temperature of the tablet bed between 35–40° C. The spraying process was stopped at a weight gain of 10–13 mg per tablet, forming the impermeable coat. A drug overcoat was applied over the insoluble coat. The drug overcoat solution was 2.5 wt. % Eudragit E100 (Rhom Pharma Ltd.) and 1.25 wt. % tizanidine dissolved in ethanol. This solution was sprayed on to the ethylcellulose coated tablets to a weight gain of 12 mg giving a drug content of 4 mg for this layer.

Results

Figure 9:
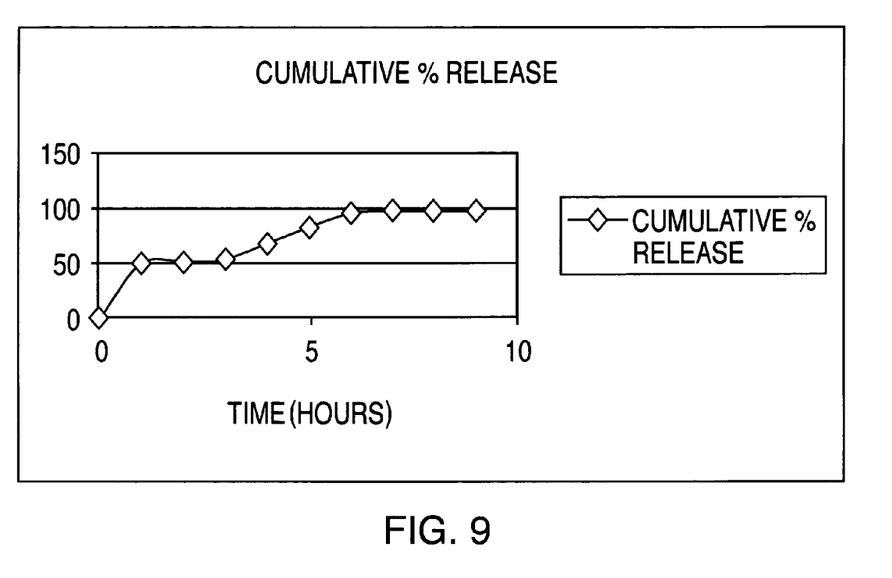
FIG. 9 shows the in vitro release profile of tizanidine from a drug delivery device made according to Example 6.

The tablets were tested in a Hanson dissolution bath at 37 C. in 900 ml of media. The first two hours were tested in 0.1N HCl. After two hours the tablets were transferred to distilled water. The tizanidine in the samples was determined by an HPLC method on a C-18 column using an aqueous buffer (pH 7.4): methanol system with UV detection at 230 nm. The results are shown in FIG. 9.

The first dose of drug, which is released immediately, is followed by a three hour delay and then a zero order release profile. When the placebo layer is thicker, the delay is longer.

Thus, a drug delivery device is described that gives good control over the time interval between the original burst of drug and a subsequent controlled release of the drug.

EXAMPLE 7

Human PK Trial of Methylphenidate

Materials and Methods

The tablets described in Example 5 were used in this Pharmacokinetic study.

Protocol Synopsis

Protocol Title:

A Single-Dose, Pharmacokinetic study of Methylphenidate HCl (36 mg) in Healthy, Male Volunteers Introduction:

Concerta® (Alza Pharmaceuticals) is a once-daily tablet formulation of Ritalin® (methylphenidate HCl), for the treatment of attention deficit/hyperactivity disorder (AD/HD) in children. AD/HD, the most commonly diagnosed behavioral disorder in children, with prevalence estimates ranging from 3–7% of school-age children, is typically treated pharmacologically, as well as with psychosocial therapies. Among the AD/HD medications prescribed are psychostimulants [such as methylphenidate HC1, dextroamphetamine (Dexedrine®), and amphetamine salts (Adderall®)]; tricyclic antidepressants; as well as neuroleptics, tranquilizers and mood stabilizers, as adjunctive medications.

However, methylphenidate HCl is by far the most widely prescribed medication, with reports of about 70–90% of AD/HD patients responding positively. Methylphenidate HC1, a mild central nervous system stimulant derived synthetically from amphetamine, and available since the mid-1970's for the treatment of AD/HD, has been shown to decrease impulsivity and hyperactivity, increase attention, and in some children, decrease aggression. Clinical improvement following methylphenidate use has been demonstrated in laboratory cognitive scales, classroom measures of disruption and academic completion, teacher ratings, parent-child interactions, and peer relationships.

Prior to the launch of Concerta®, in the fall of 2000, methylphenidate HCl was typically administered as an immediate release tablet of 5, 10 or 20 mg, 2–3 times daily. Immediate release (IR) methylphenidate HCl is absorbed and metabolized quickly (time to peak in children is 1.9 hours, range 0.3–4.4 hours), is excreted fairly rapidly and extensively (in children, 67% of the drug; in adults, 80%), and is effective from 1 to 4 hours following oral administration, with a pharmacokinetic half-life of 2–3 hours. Due to methylphenidate's relatively short half-life, multiple daily dosing was necessary to ensure adequate therapeutic coverage for the child throughout the school day, including after-school homework hours, and until bedtime.

As a result, there were serious limitations to methylphenidate's use. The need for midday dosing during the school day negatively contributed to poor compliance. In those schools where policy prohibited the administration of psychoactive medication by school personnel, AD/HD children were responsible themselves to take their midday pill, resulting in poor compliance and ineffective treatment. Alternatively, in schools where the health care staff was responsible to administer medication, midday visits to the clinic isolated AD/HD children, stigmatizing them among their peers, as well as imposing upon the school the responsibility of handling a DEA-controlled substance.

The availability, therefore, of a once-a-day dosing formulation of methylphenidate that is clinically effective, by providing a burst release followed by an ascending dosage of methylphenidate up to about 8 hours, that simulates daily dosing of three immediate-release methylphenidate tablets, as is seen in Concerta®, clearly offers substantial benefits for AD/HD patients and their health-care providers.

Study Background

The Teva R&D Initiative Group, Jerusalem, Israel recently developed a generic version of the Concerta® tablet, using a proprietary tablet formulation, called "CARP"—Controlled Area Release Plug. In the generic version, 36 mg of methylphenidate HCl is released over 12–18 hours through erosion of the multiple active drug/matrix layers though a defined geometric space. In vitro test results for the R&D Initiative formulation indicate that effectively 20% of drug is released immediately from the overcoat within 1–2 hours, followed by 60–70% release over the 8–10 hours, with a final 10–20% until hours 12–16.

This correlates quite nicely with the release profile exhibited by Concerta®, in which Alza's Oros® osmotic pressure system is used to deliver methylphenidate HCl at a controlled rate. The in vivo drug release for the current Concerta® formulation (36 mg) is essentially a biphasic ascending profile, in which there is an initial maximum concentration at about 1–2 hours, with a gradual increase in levels over the next several hours. Peak plasma concentrations are achieved at about 6–8 hours, followed by a gradual decrease in plasma levels. The overall result is a release of clinically effective plasma levels of methylphenidate over 12–14 hours following initial dosing, with the relative bioavailability of Concerta® comparable to three times a day dosing of immediate-release methylphenidate, but with fewer fluctuations between peak and trough concentrations, as compared to IR dosing.

Study Rationale

The pilot pharmacokinetic study is being conducted to evaluate whether the in vitro release profile observed for the methylphenidate HCl once-daily generic version, can be reproduced in an in vivo system.

The pharmacokinetic data to be evaluated include the $C_{max}$, $T_{max}$, and AUC (area under the plasma concentration versus time curve) following single dosing of the generic once-daily methylphenidate HCl formulations. The assay will evaluate the levels of the methylphenidate (racemic version) and its main metabolite, ritanilic acid (PPA, piperidine acetic acid).

Previous food effect studies of Concerta(®) indicate that food does not impede drug absorption and that the Concerta® may be administered in the fed or fasted state. Thus, the food effect of the once-daily methylphenidate HCl generic version will also be evaluated.

Study Objective

The objective of this study is to measure the pharmacokinetics of generic methylphenidate HCl once-daily tablets (36 mg; Teva R&D Initiative), in healthy, adult male volunteers following single dose administration. The pharmacokinetic profiles ($C_{max}$, $T_{max}$, AUC) will be evaluated under both fasted and fed conditions.

Study Design

Single-center, 2 period, pharmacokinetic study in 12 healthy male volunteers. The first period will be conducted under fasted conditions, while the second period will be conducted under fed conditions.

Study Duration

Two treatment periods separated by a minimum 1 week wash-out period between period. Each treatment period will be comprised of the following:
I. An in-patient overnight stay from the evening prior to study dosing;
II. Hourly blood sampling for 12 hours following dosing; and
III. Return to clinic following morning for final 24 hour sample.

Subjects

Twelve healthy, non-smoking, male volunteers, ages 18–40. Subjects must be in good general health with no concurrent medical conditions. Subjects may not be taking any other concomitant medications during the entire study.

Dosing Regimen:

All subjects will receive the test 2 treatment periods, with each treatment period, separated by a 1 week wash-out phase. The test article will be administered during the first period under fasting conditions, i.e., first thing in the AM, on an empty stomach, following an overnight fast of at least 10 hours.

The test article will then be administered during the second period, under fed conditions, i.e., 30 minutes after a standard, high-fat breakfast, following an overnight fast of at least 10 hours. In both periods, the treatments will be administered together with 1 glass (240 ml) water.

Sample Collections and Study Assessments

At each treatment period, blood for pharmacokinetic analysis will be collected via indwelling intravenous cannula. Whole blood (7 ml) will be collected in labeled vacutainers containing K-EDTA at 0 hour pre-dosing, and then at 15, 30, 60, and 90 minutes, 2, 3, 4, 6, 8, 10, 12, 14, 17, 20, and 24 hours post-dosing (total 16 samples). The blood will be collected at 4° C. to prevent ex vivo methylphenidate degradation. Immediately after collection, samples will be centrifuged at 1500×g for 10 minutes, and the plasma will be removed, divided into two aliquots, and placed separately into polypropylene vials and stored frozen (−20° C.) at the study site. At least 1 set of labeled aliquots will be shipped for analysis from the study site to the analytical laboratory, Anapharm Inc., Quebec, Canada, for assay. The samples should be packaged in sufficient dry ice to ensure that the samples remain frozen for at least 72 hours. The remaining set of aliquots will remain in the freezer at the clinical facility, until further notification from the Sponsor.

The samples collected will be analyzed at Anapharm Inc., using a validated high-performance liquid chromatography tandem mass spectrometry (LC/MS/MS) method in plasma, to determine the concentrations of methylphenidate HCl (racemate) and its main metabolite, ritanilic acid (PPA). The lower limits of detection (LLD) for methylphenidate and its metabolite will be determined by the analytical laboratory.

The chromatographic data will be processed at Anapharm. The audited results of the sample analysis will be provided by Anapharm in a tabular form to the Sponsor. For each session, for each subject, the $C_{max}$ (maximum concentration) and $T_{max}$ (time of maximum concentration) will be determined by inspection of the concentration versus time curves. The values obtained for the $C_{max}$ and $T_{max}$ for all subjects within a treatment group will be averaged, and the mean $C_{max}$ and $T_{max}$ calculated. Similarly, the AUC values for each subject for each session will be assessed and a mean AUC per treatment arm (fed vs. fasted), will be calculated for comparison.

It should be noted that although the study itself will not be blinded, i.e., both the subject and investigator will be aware which treatment the subject is receiving, the blood samples collected will be coded, so that the analyst at Anapharm Inc. performing the assay will be blinded. This will ensure that no bias is introduced in the study analysis.

Safety Evaluations

A routine biochemistry, hematology and urinalysis will be conducted at screening (within 21 days of the study) to ensure subject eligibility, and again, at study termination, following the last treatment period, to ensure that there has been no change as a result of the study treatments. Vital signs and a brief physical examination will be conducted at screening and at study termination; additionally, vital signs will be checked prior to each dosing period. The pre-study screening evaluation will also include a one-time HIV screen, hepatitis B, C screen, as well as a drugs of abuse screen (to be repeated prior to each study session). All subjects determined to be eligible on the basis of the above noted physical exam and screening laboratory tests, will receive an electrocardiogram prior to the study.

During the study, subjects will be observed by clinic personnel for any adverse reactions that may arise during the treatment sessions. The primary adverse events associated with chronic methylphenidate dosing are nervousness, insomnia and appetite suppression. During pharmacokinetic studies of the reference article, Concerta®, headache, nausea, dizziness and somnolence were the adverse events reported. All adverse events noted will be reported and recorded.

Study Expectations

It is expected that the pharmacokinetic profiles ($T_{max}$, $C_{max}$, and AUC) for once-daily methylphenidate HCl following dosing in either fed or fasted conditions will be similar to literature data for Concerta® and that there will be no significant food effect evident.

Results

Figure 10A:
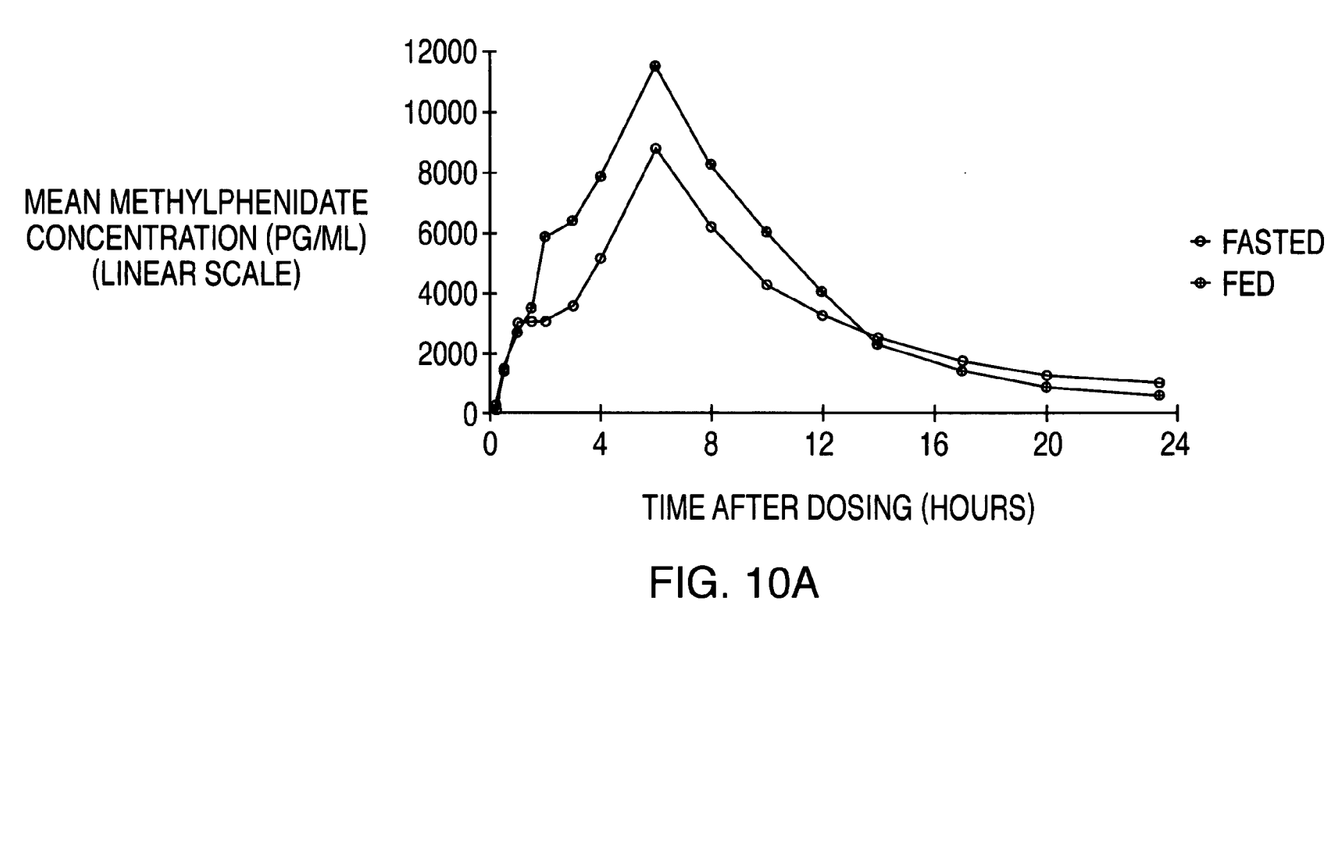
FIGS. 10(a) and 10(b) show the mean plasma methylphenidate concentrations following single dose oral administration of a 36 mg methylphenidate tablet (CARP ; Teva R & D ; Test) to twelve healthy male Caucasian volunteers in the fed and fasting states.
Figure 10B:
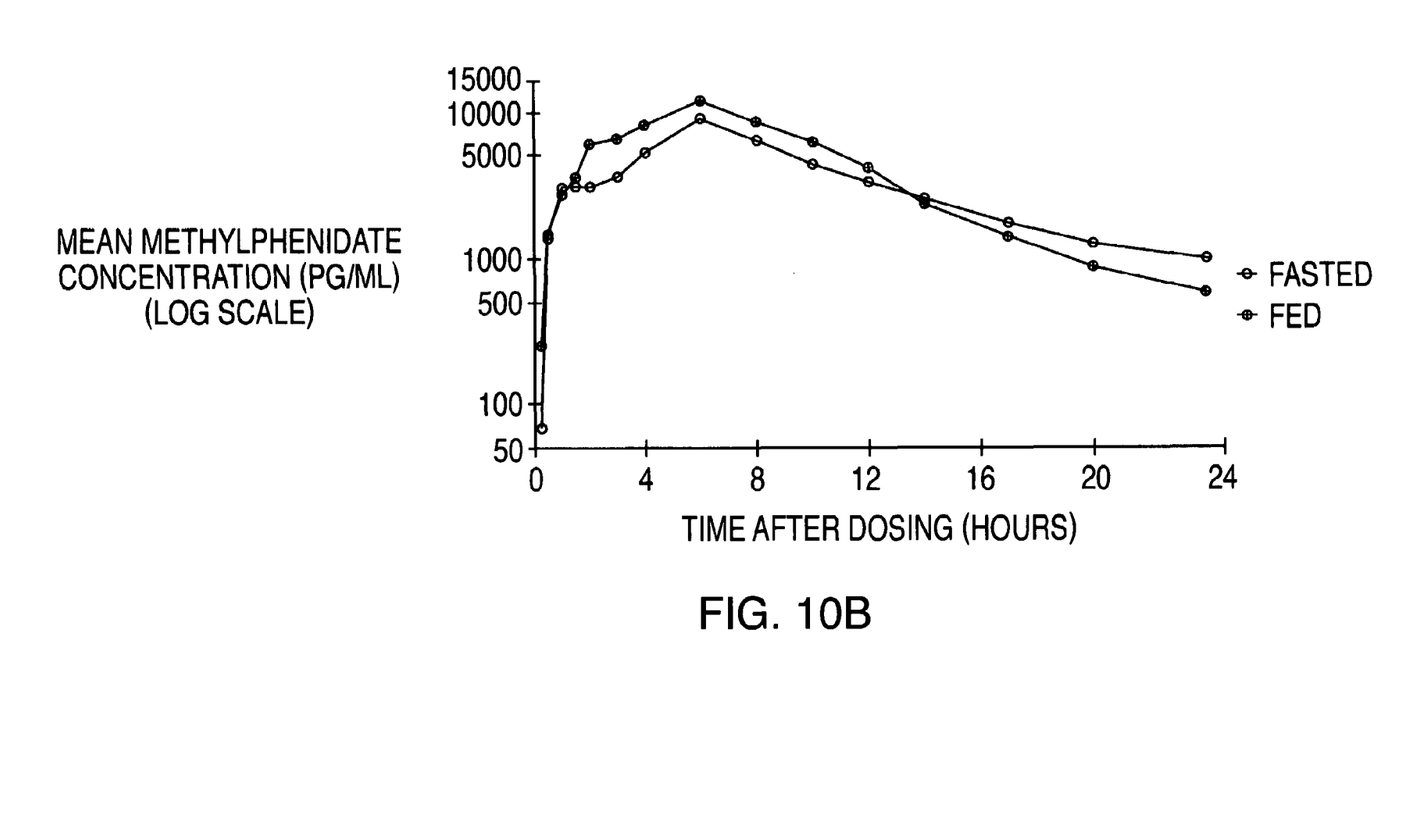

The pharmacokinetic results of the trial are summarized in Table 17. The graphs of the average concentrations of methylphenidate for all volunteers in the fed and fasted state are given in FIGS. 10a and b. A comparison of the results to literature results for Concerta® are given in Table 18.

TABLE 17

Pharmacokinetic Parameters for Fed and Fasted Administration of CARP Methylphenidate

| vol-sess | AUC (h*pg/g) | AUC inf | t1/2 | CL | Vd | Tmax (h) | Cmax (pg/g) |
|---|---|---|---|---|---|---|---|
| sub-02-fast | 135768.7 | 146764.0 | 5.5 | 0.3 | 2.1 | 6.0 | 16813.0 |
| sub-04-fast | 71622.3 | 78448.6 | 6.5 | 0.5 | 4.7 | 6.0 | 8894.0 |
| sub-05-fast | 57939.6 | 84075.0 | — | 0.6 | — | 6.0 | 3181.0 |
| sub-06-fast | 89305.1 | 90413.0 | 3.2 | 0.4 | 1.9 | 6.0 | 12980.0 |

TABLE 17-continued

Pharmacokinetic Parameters for Fed and Fasted Administration of CARP Methylphenidate

| vol-sess | AUC (h*pg/g) | AUC inf | t1/2 | CL | Vd | Tmax (h) | Cmax (pg/g) |
|---|---|---|---|---|---|---|---|
| sub-10-fast | 69621.3 | 87148.8 | 8.0 | 0.5 | 6.0 | 6.0 | 5597.0 |
| sub-11-fast | 59955.3 | 66837.1 | 6.4 | 0.6 | 5.5 | 8.0 | 4437.0 |
| sub-01-fast | 76974.8 | 76974.8 | 6.2 | 0.5 | 4.2 | 6.0 | 7638.0 |
| sub-03-fast | 79199.1 | 94600.1 | 8.4 | 0.5 | 5.5 | 6.0 | 9126.0 |
| sub-07-fast | 79263.1 | 82754.1 | 4.6 | 0.5 | 3.0 | 4.0 | 8323.0 |
| sub-08-fast | 43951.9 | 46616.6 | 4.8 | 0.8 | 5.7 | 6.0 | 5429.0 |
| sub-09-fast | 112308.0 | 115488.7 | 3.9 | 0.3 | 1.8 | 6.0 | 16315.0 |
| sub-12-fast | 83772.8 | 89946.2 | 4.2 | 0.4 | 2.6 | 6.0 | 9190.0 |
| sub-01-fed | 84269.0 | 85450.6 | 2.9 | 0.4 | 1.8 | 6.0 | 15547.0 |
| sub-03-fed | 105656.9 | 108586.5 | 3.8 | 0.3 | 1.9 | 6.0 | 15430.0 |
| sub-07-fed | 78667.1 | 82765.7 | 4.0 | 0.5 | 2.7 | 10.0 | 8082.0 |
| sub-08-fed | 73960.2 | 74582.1 | 3.0 | 0.5 | 2.1 | 2.0 | 12273.0 |
| sub-09-fed | 99874.5 | 102764.8 | 3.9 | 0.4 | 2.1 | 8.0 | 10649.0 |
| sub-12-fed | 96907.6 | 110862.0 | 5.7 | 0.4 | 3.1 | 4.0 | 12291.0 |
| sub-02-fed | 168704.9 | 172355.0 | 3.5 | 0.2 | 1.1 | 2.5 | 21000.0 |
| sub-04-fed | 110300.6 | 111340.3 | 2.7 | 0.3 | 1.3 | 6.0 | 21000.0 |
| sub-05-fed | 111532.3 | 114982.0 | 3.4 | 0.3 | 1.6 | 10.0 | 10378.0 |
| sub-06-fed | 103398.1 | 105050.0 | 3.0 | 0.3 | 1.5 | 6.0 | 14265.0 |
| sub-10-fed | 96652.2 | 98841.7 | 3.2 | 0.4 | 1.7 | 6.0 | 12803.0 |
| sub-11-fed | 66807.2 | 69717.3 | 4.7 | 0.5 | 3.7 | 4.0 | 9452.0 |
| AVG(fast) | 79973.5 | 88338.9 | 5.6 | 0.5 | 3.9 | 6.0 | 8993.6 |
| AVG (fed) | 99727.6 | 103108.2 | 3.7 | 0.4 | 2.0 | 5.9 | 13597.5 |
| geomn(fast) | 76778.9 | 85317.8 | 5.4 | 0.5 | 3.6 | 5.9 | 8034.9 |
| geomn(fed) | 97010.5 | 100345.7 | 3.6 | 0.4 | 1.9 | 5.3 | 13059.3 |
| stddev(fast) | 24552 | 24638 | 1.7 | 0.1 | 1.7 | 0.9 | 4388 |
| stddev(fed) | 26121 | 26578 | 0.9 | 0.1 | 0.8 | 2.6 | 4134 |

TABLE 18

Comparison of Parmacokinetic Parameters of Methylphenidate CARP to Literature Parameters for Concerta ®

| Fasted/fed | Parameter | CARP (36 mg) mean | SD | Concetrta ® (Literature*) mean | SD | ratio |
|---|---|---|---|---|---|---|
| fasted | Cmax (ng/ml) | 9.00 | 4.39 | 6.20 | 2.20 | 145.2% |
| fed | Cmax (ng/ml) | 13.60 | 4.13 | 6.87 | 2.30 | 198.0% |
| | ratio | 151.1% | | 110.8% | | |
| fasted | AUCI (ng.h/ml) | 88.34 | 24.63 | 67.6 | 23.70 | 130.7% |
| fed | AUCI (ng.h/ml) | 103.11 | 26.58 | 79.0 | 26.80 | 130.5% |
| | ratio | 116.72% | | 116.9% | | |

*Modi NB et. al. Effect of food on the pharmacokinetics of osmotic controlled release methylphenidate HCl in healthy subjects. Biopharmaceutics and Drug Disposition, (2000), 21, 23—31

The results of this trial show methylphenidate release into the plasma at amounts and rates similar to that of Concerta®. The total amount of methylphenidate found in each volunteer as expressed by the area under the concentration time curve extrapolated to infinity ($AUC_{inf}$) ranged from ranged from 47 to 147 h*ng/g for the fasted subjects and from 70 to 172 h*ng/g for the fed subjects, with an average value of 88 and 103 h*ng/g respectively. The maximum concentrations found in the plasma ranged from 3.2 ng/g to 16.8 ng/g for the fasted subjects and 8.1 to 21.0 ng/g for the fed subjects, with respective averages of 9.0 and 13.6 ng/g. The time of maximum concentration ranged from 4 to 8 hours (with 10 of twelve subjects having $T_{max}$ at 6 hours) in the fasted subjects and from 2 to 10 hours in the fed subjects. The average $T_{max}$ was 6.0 for the fasted subjects and 5.9 for the fed subjects. The half life of elimination ranged from 3.2 to 8.4 hours in the fasted subjects and 2.7 to 5.7 hours in the fed subjects with averages of 5.6 and 3.7 hours respectively.

Comparisons of these values to those of literature values of Concerta® did not show bioequivalence but the results are close and encouraging for a pilot trial.

CONCLUSIONS

The results show a successful in vivo profile of controlled release of methylphenidate. As designed, and seen in vitro, the in vivo profile shown in FIGS. 10(a) and (b) is one of an initial burst of drug followed, after a delay, by an extended release that gives an ascending profile in the plasma. This confirms the usefulness of this drug delivery device for providing complicated drug delivery profiles.

What is claimed is:

1. A drug delivery device, comprising:
a core comprising a drug;
a cylindrical plug embedded in the core, wherein said cylindrical plug comprises a swellable material; and
a coating at least partially surrounding the core and covering the plug, wherein
said coating is essentially impermeable to the drug, and said plug punctures
said coating upon swelling of said plug, thereby forming an orifice in said coating.

2. The drug delivery device of claim 1, wherein the cylindrical plug is hollow.

3. The drug delivery device of claim 1, wherein the cylindrical plug is solid.

4. The drug delivery device of claim 2, wherein the outer diameter of the hollow cylindrical plug ranges from about 5 mm to about 9 mm.

5. The drug delivery device of claim 2, wherein the inner diameter of the hollow cylindrical plug ranges from about 1 mm to about 6 mm.

6. The drug delivery device of claim 4, wherein the outer diameter of the hollow cylindrical plug is about 7 mm.

7. The drug delivery device of claim 5, wherein the inner diameter of the hollow cylindrical plug ranges from about 2 mm to about 3 mm.

8. The drug delivery device of claim 1, wherein the core comprises a material which dissolves or erodes upon contact with a fluid.

9. The drug delivery device of claim 1, wherein the core comprises sucrose, polyethylene glycol 8000, microcrystalline cellulose and magnesium stearate.

10. The drug delivery device of claim 1, wherein the swellable material is a hydrogel.

11. The drug delivery device of claim 10, wherein the hydrogel is selected from the group consisting of hydroxypropylcellulose, hydroxypropylmethylcellulose, methylcellulose, polyvinylpyrrolidone, polyethylene oxide, and mixtures thereof.

12. The drug delivery device of claim 1, wherein the cylindrical plug further comprises a disintegrant.

13. The drug delivery device of claim 12, wherein the disintegrant is a superdisintegrant selected from the group consisting of croscarmellose sodium, crospovidone, sodium starch glycolate and mixtures thereof.

14. The drug delivery device of claim 1, wherein the coating which is essentially impermeable to the drug comprises ethylcellulose.

15. The drug delivery device of claim 1, comprising a drug coating over the impermeable coating.

16. The drug delivery device of claim 15, wherein the drug coating is a fast dissolving coating that provides an immediate release of the drug in the coating.

17. The drug delivery device of claim 15, wherein the drug coating is one that erodes and provides a sustained release of the drug in the coating.

18. The drug delivery device of claim 16, wherein the drug coating comprises a material that dissolves in the stomach.

19. The drug delivery device of claim 17, wherein the drug coating comprises polyvinylpyrrolidone, hydroxypropylcellulose, hydroxypropylmethylcellulose or mixtures thereof.

20. The drug delivery device of claim 1, which has a zero order drug release profile.

21. The drug delivery device of claim 15, which has a biphasic drug release profile.

22. The drug delivery device of claim 1, which has an ascending drug release profile.

23. The drug delivery device of claim 1, which has a descending drug release profile.

24. The drug delivery device of claim 21, wherein during the first phase the drug release profile is zero order and during the second phase drug is released at a faster than zero order release rate.

25. The drug delivery device of claim 21, wherein the first phase is characterized by a slow release and the second phase is characterized by a rapid release.

26. The drug delivery device of claim 21, wherein the first phase provides immediate release of the drug and the second phase provides a delayed release of the drug.

27. The drug delivery device of claim 1, wherein the drug is selected from the group consisting of acetaminophen, oxybutynin, methylphenidate, tizanidine and copaxone.

28. The drug delivery device of claim 1, wherein the cylindrical plug is a bi-layered tablet.

29. The drug delivery device of claim 28, further comprising a drug coating over the impermeable coating.

30. The drug delivery device of claim 29, wherein at least one of the layers of the bi-layer tablet contains a drug, which may be the same or different as that in the core.

31. The drug delivery device of claim 30, which has a triphasic drug release profile.

32. The drug delivery device of claim 31, wherein the first phase provides immediate release of the drug and the second and third phases provide a delayed release of the drug.

33. The drug delivery device of claim 30, wherein the drug coating provides for immediate release of the drug.

34. The drug delivery device of claim 28, wherein one of the layers is a placebo layer that is capable of bursting through the impermeable coating, and the other layer contains a drug.

35. The drug delivery device of claim 34, wherein the drug in the core, bi-layer tablet and drug coating is methylphenidate.

36. The drug delivery device of claim 35, wherein the drug in the core is released in an extended zero-order release fashion.

37. The drug delivery device of claim 1, wherein the core is a bi-layer tablet.

38. The drug delivery device of claim 26, wherein the drug in the core and the drug in the drug coating is tizanidine.

39. A method of making a drug delivery device comprising:
forming a core comprising a drug;
embedding a cylindrical plug in the core, wherein said cylindrical plug comprises a swellable material; and at least partially coating the core and covering the plug with a coating which is essentially impermeable to the drug, wherein said plug punctures said coating upon swelling of said plug, thereby forming an orifice in said coating.

40. The method of claim 39, wherein the core and the cylindrical plug are compressed together.

41. The method of claim 39, wherein the compression is done on a press coat tableting machine.

42. The method of claim 41, wherein the core is fed into the press coat tableting machine as a mixture of powders or granulates.

43. The method of claim 39, wherein the cylindrical plug is hollow.

44. The method of claim 39, wherein the cylindrical plug is solid.

* * * * *